United States Patent [19]
Eberlein et al.

[11] 3,949,074
[45] Apr. 6, 1976

[54] CARDIOTONIC PHARMACEUTICAL COMPOSITIONS CONTAINING A CARDIAC GLYCOSIDE AND METHOD OF USE

[75] Inventors: Wolfgang Eberlein, Mettenberg; Joachim Heider, Warthausen-Oberhofen; Willi Diederen, Rissegg, all of Germany; Walter Kobinger, Vienna, Austria

[73] Assignee: Boehringer Ingelheim GmbH, Ingelheim am Rheim, Germany

[22] Filed: Aug. 4, 1975

[21] Appl. No.: 601,500

[30] Foreign Application Priority Data
Sept. 18, 1972 Germany.................... 2245726

Related U.S. Application Data
[62] Division of Ser. No. 397,852, Sept. 17, 1973.

[52] U.S. Cl............................ 424/182; 260/210.5
[51] Int. Cl.²..................................... A61K 31/705
[58] Field of Search..................................... 424/182

[56] References Cited
UNITED STATES PATENTS
3,752,803   8/1973   Eberlein et al..................... 424/182

*Primary Examiner*—Lewis Gotts
*Assistant Examiner*—Cary Owens
*Attorney, Agent, or Firm*—Hammond & Littell

[57] ABSTRACT

Pharmaceutical compositions containing as an active ingredient a compound of the formula

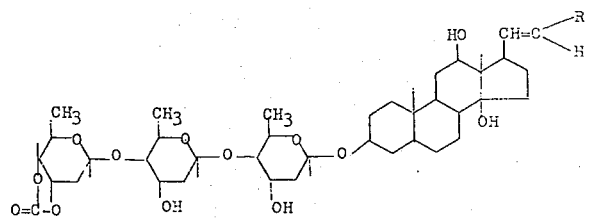

wherein R is cyano or carbalkoxy of 2 to 4 carbon atoms; and a method of using the same as cardiotonics.

8 Claims, No Drawings

CARDIOTONIC PHARMACEUTICAL COMPOSITIONS CONTAINING A CARDIAC GLYCOSIDE AND METHOD OF USE

This is a division of copending application Ser. No. 397,852 filed Sept. 17, 1973.

This invention relates to novel pharmaceutical compositions containing a cardiac glycoside, and to a method of using the same as cardiotonics.

More particularly, the present invention relates to novel cardiotonic dosage unit compositions consisting essentially of an inert pharmaceutical carrier and an effective cardiotonic amount of a compound of the formula

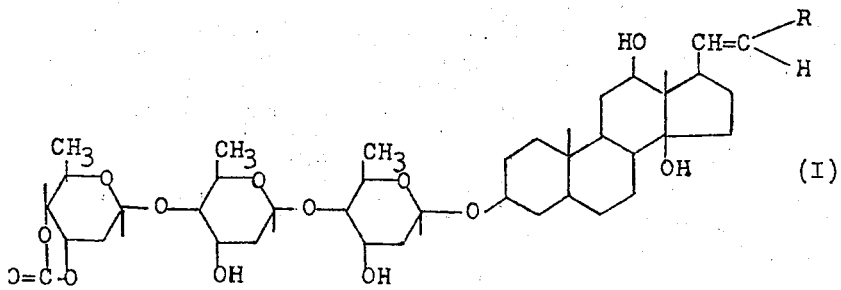

wherein R is cyano or carbalkoxy of 2 to 4 carbon atoms, preferably methoxycarbonyl.

The compounds embraced by formula I may be prepared by reacting a compound of the formula

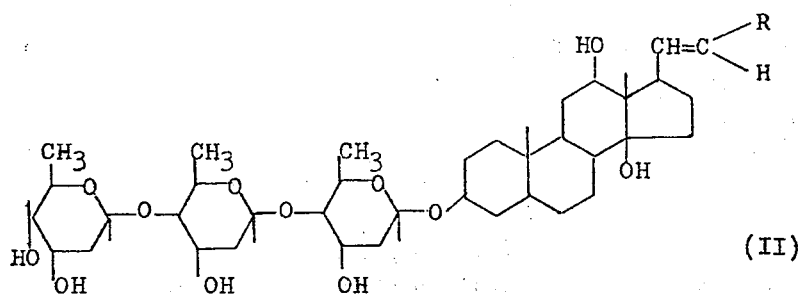

wherein R has the same meanings as in formula I, with a compound of the formula

(III)

wherein X is halogen, imidazolidyl, lower alkoxy, aryl-lower alkoxy or aryloxy, in an inert organic solvent, such as ether, dioxane, tetrahydrofuran, methylene chloride, dichloroethane or dimethylformamide, and optionally in the presence of a tertiary organic base, such as triethylamine or pyridine.

When X in formula III is halogen, the reaction is preferably performed in the presence of a tertiary organic base, such as triethylamine or pyridine; if the tertiary organic base is a liquid at the reaction temperature and is provided in sufficient excess, it may simultaneously serve as the solvent medium for the reaction. The reactant of the formula III is advantageously provided in excess over the stoichiometrically required amount. The reaction temperature may vary between −60°C and the boiling point of the particular solvent medium which is used, but the reaction is preferably performed at a temperature between −20° and +20°C.

When X in formula III is imidazolidyl, the reaction is preferably carried out with one mol-equivalent of a compound of the formula III and within the temperature range of 0° and 100°C, preferably at the boiling point of the solvent medium.

The starting compounds of the formulas II and III are described in the literature (see Belgian Pat. No. 774,509 and U.S. Pat. No. 3,752,803). For instance, a compound of the formula II is obtained by reacting 3β-(tridigitoxosyltetraacetate)-12β-acetoxy-14β-hydroxy-17β-formyl-5β-androstane with diethylphosphono-acetonitrile or the corresponding diethylphosphonoacetic acid ester in the presence of a base, such as potassium tert.butylate, and subsequently removing the four protective acetyl sustituents.

The following examples illustrate the preparation of compounds of the formula I.

EXAMPLE 1

3-(3′-β-Tridigitoxosyl-12′β,14′β-dihydroxy-5′β-androstan-17′β-yl)-acrylonitrile 3‴,4‴-carbonate A solution of 1.5 gm (1.9 millimols) of 3-(3′β-tridigitoxosyl-12′β,14′β-dihydroxy-5′β-androstan-17′β-yl(-acrylonitrile in 75 ml of pyridine was admixed dropwise with 18 ml of a 10% solution of phosgene in toluene, while cooling the mixture on an ice bath. The resulting mixture was stirred for one hour more at 0°C and was then poured into 200 ml of ice water. The resulting aqueous mixture was extracted several times with chloroform, and the combined organic extracts were washed successively with dilute hydrochloric acid, a saturated aqueous sodium bicarbonate solution and water, dried over sodium sulfate and evaporated to dryness in a rotary evaporator. The residue was chromatographed on 200 gm of activated silicagel with chloroform/acetone (6:1 to 2:1), yielding 530 mgm (25.6% of theory) of the compound of the formula

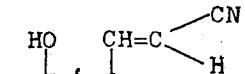
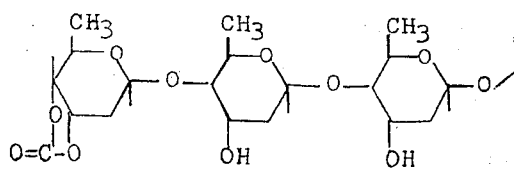

which had a melting point of 250°–252°C after being recrystallized twice from chloroform/cyclohexane. $R_f$ Value: 0.45 (flow agent: ethyl acetate)

IR-Bands (solid in KBr) : 3400–3550 cm$^{-1}$ (—OH), 2230 cm$^{-1}$ (—CN), 1810 cm$^{-1}$ (carbonate), 1625 cm$^{-1}$ (—C=C—).

EXAMPLE 2

Using a procedure analogous to that described in Example 1, 620 mgm (30% of theory) of pure methyl 3-(3′β-tridigitoxosyl-12′β,14′β-dihydroxy-5′β-androstan-17′β-yl)-acrylate 3‴,4‴-carbonate, m.p. 225°–227°C (recrystallized from chloroform/cyclohexane), of the formula

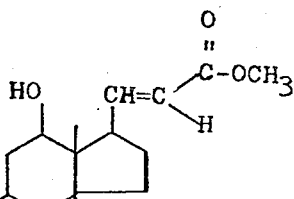
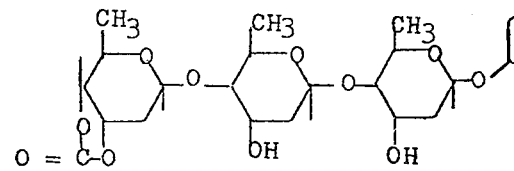

were obtained from 1.5 gm (1.9 millimols) of methyl 3-(3′β-trdigitoxosyl-12′62 ,14′β-dihydroxy-5′β-androstan-17′β-yl)-acrylate and 18 ml of a 10% solution of phosgene in toluene. $R_f$-Value: 0.45 (flow agent: ethyl acetate)

IR-Bands (solid in KBr): 3350–3200 cm$^{-1}$ (—OH), 1810 cm$^{-1}$ (carbonate —C=O), 1715 cm$^{-1}$ (ester —C=O), 1630 cm$^{-1}$ (—C=C—).

The compounds embraced by formula I have useful pharmacodynamic properties. More particularly, they exhibit cardiotonic and especially positive inotropic activities in warm-blooded animals, such as cats and guinea pigs. The compounds of the present invention are further characterized by a very favorable oral absorption rate, as well as by a very favorable rate of elimination which corresponds to that of g-strophanthin, whereby the danger of cumulation and occurrence of intoxication symptoms is reduced.

For instance, the more favorable absorption rate of 3-(3′β-tridigitoxosyl)-12′β,14′β-dihydroxy-5′β-androstan-17′β-yl)-acrylonitrile 3‴,4‴-carbonate (A) according to the present invention in comparison to the prior art precursor 3-(3′β-tridigitoxosyl)-12′β,-14′β-dihydroxy-5′β-androstan-17′β-yl)-acrylonitrile (B) was ascertained by the following tests:

1. Infusion toxicity in cats:

The compound under investigation was intravenously infused into cats of 2–3 kg body weight under pentobarbital anesthesia (30 mgm/kg i.v.), while administering artificial respiration ([see R. A. Hatcher et al, Am. J. Pharmac. 82, 360 (1910)]. The infusion rate was chosen to be such that death due to heart failure occurred after 50 to 60 minutes, and from the raw data the average absolute lethal dose ($LD_{100}$) was calculated. The following table shows the results obtained.

TABLE I

| Compound | Number of animals | $LD_{100}$ mgm/kg i.v. |
|---|---|---|
| Invention: A | 8 | 338 |
| Prior art: B | 4 | 528 |

2. Enteral absorption rate in rats

The enteral absorption rate was determined for each test compound by way of the K$^+$-elimination in the urine of rats, by determining those doses which, after intravenous administration, produced the same K$^+$-elimination as after peroral administration within a period of two hours [see Arch. Path, and Pharmakol. 233, 468 (1958)]. The following table shows the results obtained.

TABLE II

| Compound | Enteral absorption rate after 2 hours |
|---|---|
| Invention: A | 100% |
| Prior art: B | 40% |

For pharmaceutical purposes the compounds of the formula I are administered to warm-blooded animals perorally or parenterally as active ingredients in customary dosage unit compositions, that is, compositions in dosage unit form consisting essentially of an inert pharmaceutical carrier and one effective dosage unit of the active ingredient, such as tablets, coated pills, capsules, wafers, powders, solutions, suspensions, emulsions, syrups, suppositories and the like. One effective dosage unit of the compounds according to the present invention is from 0.002 to 0.034 mgm/kg body weight.

The following examples illustrate a few pharmaceutical dosage unit compositions comprising a compound of the formula I as an active ingredient and represent the best modes contemplated of putting the invention into practical use. The parts are parts by weight unless otherwise specified.

EXAMPLE 3

Tablets

The tablet composition is compounded from the following ingredients:

| | | |
|---|---|---|
| 3-(3'β-Tridigitoxosyl-12'β,14'β-dihydroxy-5'β-androstan-17'β-yl)-acrylonitrile 3''',4'''-carbonate | 0.25 | parts |
| Lactose | 85.75 | " |
| Potato starch | 30.00 | " |
| Gelatin | 3.00 | " |
| Magnesium stearate | 1.00 | " |
| Total | 120.00 | parts |

Preparation:

The acrylonitrile compound is intimately admixed with 2.5 parts of lactose, the mixture is admixed with the remainder of the lactose and the potato starch, the resulting mixture is moistened with an aqueous 10% solution of the gelatin, the moist mass is forced through a 1.5 mm-mesh screen, the resulting granulate is dried at 40°C and again passed through a 1 mm-mesh screen, the dry granulate is admixed with the magnesium stearate, and the composition is compressed into 120 mgm-tablets in a conventional tablet making machine. Each tablet contains 0.25 mgm of the acrylontrile compound and is an oral dosage unit composition with effective positive inotropic cardiotonic action.

EXAMPLE 4

Coated pills

The pill core composition is compounded from the following ingredients:

| | | |
|---|---|---|
| 3-(3'β-Tridigitoxosyl-12'β,14'β-dihydroxy-5'β-androstan-17'β-yl)-acrylonitrile 3''',4'''-carbonate | 0.25 | parts |
| Lactose | 32.25 | " |
| Corn starch | 15.00 | " |
| Polyvinylpyrrolidone | 2.00 | " |
| Magnesium stearate | 0.50 | " |
| Total | 50.00 | parts |

Preparation:

The acrylonitrile compound is intimately admixed with 2.5 parts of lactose, the mixture is admixed with the remainder of the lactose and the corn starch, the resulting mixture is moistened with an aqueous 15% solution of the polyvinylpyrrolidone, the moist mass is forced through a 1 mm-mesh screen, the resulting granulate is dried at 40°C and again passed through the screen, the dry granulate is admixed with the magnesium stearate, and the composition is compressed into 50 mgm-pill cores which are subsequently coated with a thin shell consisting essentially of a mixture of sugar and talcum and polished with beeswax. Each coated pill contains 0.25 mgm of the acrylonitrile compound and is an oral dosage unit composition with effective positive inotropic cardiotonic action.

EXAMPLE 5

Drop solution

The solution is compounded from the following ingredients:

| | | |
|---|---|---|
| 3-(3'β-Tridigitoxosyl-14'β-hydroxy-5'β-androstan-17'β-yl)-acrylonitrile 3''',4'''-carbonate | 0.0125 | parts |
| Saccharin sodium | 0.3 | " |
| Sorbic acid | 0.1 | " |
| Ethanol | 30.0 | " |
| Flavoring | 1.0 | " |
| distilled water q.s.ad | 100.0 | " |

Preparation:

The acrylonitrile compound and the flavoring are dissolved in the ethanol, the resulting solution is admixed with a solution of the sorbic acid and the saccharin sodium in the distilled water, and the mixed solution is filtered until free from suspended matter. 1 ml (about 20 drops) of the filtrate contains 0.125 mgm of th acrylonitrile compound and is an oral dosage unit composition with effective positive inotropic cardiotonic action.

EXAMPLE 6

Hypodermic solution

The solution is compounded from the following ingredients:

| | | |
|---|---|---|
| 3-(3'β-Tridigitoxosyl-12'β,14'β-dihydroxy-5'β-androstan-17'β-yl)-acrylonitrile 3''',4'''-carbonate | 0.25 | parts |
| Polyethyleneglycol 600 | 150.00 | " |
| Tartaric acid | 5.00 | " |
| Distilled water q.s.ad | 1000.00 | " |
| | | by vol. |

Preparation:

The tartaric acid, the polyethyleneglycol and the acrylonitrile compound are successively dissolved in a sufficient amount of distilled water, and the resulting solution is diluted to the indicated volume with distilled water and then filtered until free from suspended matter. The filtrate is filled into 3 ml-ampules in an atmosphere of nitrogen, and the filled ampules are sterilized for 20 minutes at 120°C and then sealed. Each ampule contains 0.25 mgm of the acrylonitrile compound, and the contents thereof are an injectable dosage unit composition with effective positive inotropic cardiotonic action.

EXAMPLE 7

Suppositories

The suppository composition is compounded from the following ingredients:

| | | |
|---|---|---|
| 3-(3'β-Tridigitoxosyl-12'β,14'β-dihydroxy-5'β-androstan-17'β-yl)-acrylonitrile 3''',4'''-carbonate | 0.25 | parts |
| Lactose | 4.75 | " |
| Suppository base (e.g. cocoa butter) | 1695.00 | " |
| Total | 1700.00 | parts |

Preparation:

The acrylonitrile compound and the lactose are admixed with each other, the mixture is milled and then blended with the aid of an immersion homogenizer in the suppository base which had previously been melted and cooled to 40°C, and 1700 mgm-portions of the resulting composition are poured at 37°C into cooled suppository molds and allowed to harden. Each suppository contains 0.25 mgm of the acrylonitrile compound and is a rectal dosage unit composition with effective positive inotropic cardiotonic action.

Analogous results are obtained when any one of the other compounds embraced by formula I is substituted for the particular acrylic acid compound in Examples 3 through 7. Likewise, the amount of active ingredient in these illustrative examples may be varied to achieve the dosage unit range set forth above, and the amounts and nature of the inert pharmaceutical carrier ingredients may be varied to meet particular requirements.

While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

We claim:

1. A cardiotonic pharmaceutical dosage unit composition consisting essentially of an inert pharmaceutical carrier and an effective cardiotonic amount of a compound of the formula

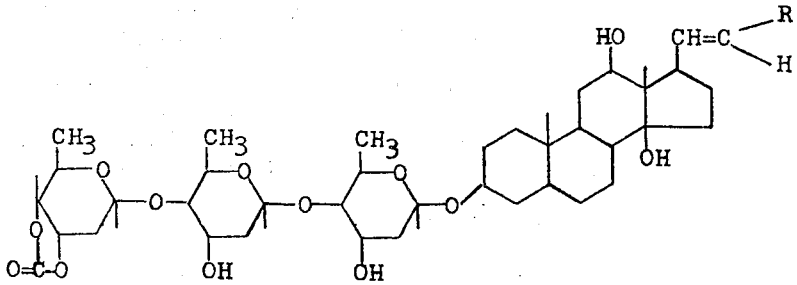

wherein R is cyano or carbalkoxy of 2 to 4 carbon atoms.

2. A composition of claim 1, where R is cyano or methoxycarbonyl.

3. The composition of claim 2, where said compound is 3-(3′β-tridigitoxosyl-12′β,14′β-dihydroxy-5′β-androstan-17′β-yl)-acrylonitrile 3′′′,4′′′-carbonate.

4. The composition of claim 2, where said compound is methyl 3-(3′β-tridigitoxosyl-12′β,14′β-dihydroxy-5′β-androstan-17′β-yl)-acrylate 3′′′,4′′′-carbonate.

5. The method of increasing the strength of cardiac muscle contraction in a warm-blooded animal in need thereof, which comprises administering to said animal an effective cardiotonic amount of a compound of the formula

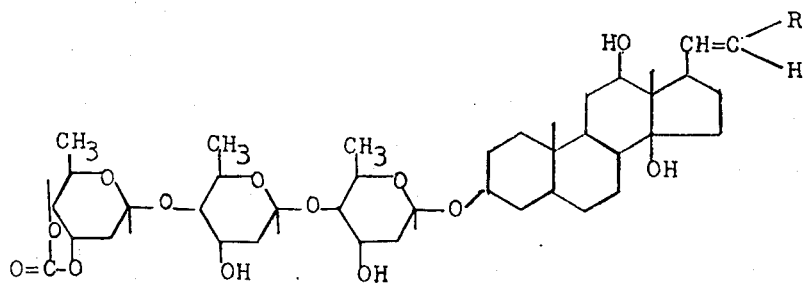

wherein R is cyano or carbalkoxy of 2 to 4 carbon atoms.

6. The method of claim 5, where R is cyano or methoxycarbonyl.

7. The method of claim 6, where said compound is 3-(3′β-tridigitoxosyl-12′β,14′β-dihydroxy-5′β-androstan-17′βyl)-acrylonitrile 3′′′,4′′′-carbonate.

8. The method of claim 6, where said compound is methyl 3-(3′β-tridigitoxosyl-12′β,14′β-dihydroxy-5′β-androstan-7′β-yl)-acrylate 3′′′,4′′′-carbonate.

* * * * *

UNITED STATES PATENT OFFICE
CERTIFICATE OF CORRECTION

Patent No. 3,949,074     Dated  April 6, 1976

Inventor(s) Wolfgang Eberlein et al.

It is certified that error appears in the above-identified patent and that said Letters Patent are hereby corrected as shown below:

Column 3, line 44, "-trdigitoxosyl-" should read

-- -tridigitoxosyl- --

Column 3, line 44, "62" should read --β--

Column 3, line 48, "3350" should read -- 3550 --.

Signed and Sealed this fifteenth Day of June 1976

[SEAL]

Attest:

RUTH C. MASON
Attesting Officer

C. MARSHALL DANN
Commissioner of Patents and Trademarks